United States Patent

Kelley

Patent Number: 5,556,631
Date of Patent: Sep. 17, 1996

[54] WATER RESISTANT PESTICIDE COMPOSITIONS

[76] Inventor: Donald W. Kelley, 608 N. Palestine, Athens, Tex. 75751

[21] Appl. No.: 315,937

[22] Filed: Sep. 30, 1994

[51] Int. Cl.⁶ .................................................. A01N 25/26
[52] U.S. Cl. .................................... 424/410; 424/418
[58] Field of Search ................................ 424/408, 410, 424/405, 403, 84, DIG. 8, DIG. 10, 418

[56] References Cited

U.S. PATENT DOCUMENTS

| | | | |
|---|---|---|---|
| 2,824,826 | 2/1958 | Katsaros et al. | 424/405 |
| 2,957,804 | 10/1960 | Shuyler | 424/410 |
| 3,186,912 | 6/1965 | Beamer | 424/DIG. 10 |
| 3,496,272 | 2/1970 | Kruger | 424/405 |
| 4,966,796 | 10/1990 | Aki et al. | 424/415 |
| 5,123,950 | 6/1992 | Homma et al. | 424/405 |
| 5,140,017 | 8/1992 | Pickford | 424/405 |
| 5,290,751 | 3/1994 | Fiard et al. | 424/405 |

FOREIGN PATENT DOCUMENTS 802781  9/1936  France.

*Primary Examiner*—Thurman K. Page
*Assistant Examiner*—P. Webber
*Attorney, Agent, or Firm*—Donald W. Erickson

[57] ABSTRACT

A solid pesticide composition such as a bait or granule which is made water resistant by coating the solid pesticide with a hydrophobic fatty acid poly ester of sucrose, sorbitol, sorbinose, glycerol and/or raffinose. The coated solid pesticide composition retains its palatability to the target pest.

20 Claims, No Drawings

WATER RESISTANT PESTICIDE COMPOSITIONS

BACKGROUND OF THE INVENTION

This invention is directed at water resistant pesticide compositions such as baits and granules.

Pesticidal baits are traditionally formulated with active pesticides and/or attractants, onto an inert substrate which is palatable to the targeted pest. Desirable inert substrates include sugar, ground corn cob, corn meal, oatmeal, etc. These substrates are water soluble or they are very hydroscopic. This property limits where the bait can be used and how long it will last, depending on the amount of moisture available. An object of this invention is to provide a means to render pesticidal baits water resistant, thereby expanding the environment in which they can be used and extending the time of their activity over that of non-water resistant pesticidal baits.

Pesticidal granules are traditionally formulated on mineral or cellulosic substrates such as clay, diatomaceous earth, silica, corn cob, peanut hulls, paper, etc. These materials tend to be hydrophylic or hydroscopic or if hydrophobic they do not adsorb liquids except on the surfaces. If the pesticides are on the surfaces they are frequently removed when placed in contact with water or they are chemically degraded reducing their useful life. If the materials are hydrophylic they tend to cake when they become wet and function as moisture trap which maintains a humid environment in their immediate area as well as degrading the pesticide. These factors become very important in outdoor equipment in that: 1.) the equipment is visited infrequently thus requiring long lasting insect control for protection of the equipment and 2.) temperature cycling creates moisture condensation, which is held and released over time by the granule to create an ideal corrosive environment in enclosed equipment. While there are numerous means of applying pesticides in such a manner that circumvent the negatives associated with granules, they are expensive and the convenience of a granule product is lost. This invention describes a means of using traditional granule materials and circumventing the moisture problems described above by making the granules water resistant or waterproof.

SUMMARY OF THE INVENTION

Water resistant pesticide compositions of the present invention can be prepared by applying the pesticide to any of the traditional solid carriers or substrates and then a high melting solid hydrophobic ester is homogeneously mixed with the carrier and heat applied melting the ester and forming a uniform hydrophobic coating on the carrier.

Some pesticide carriers such as sugar dissolve rapidly in water, pick up moisture from the air or moisture from the surface that it is in contact with. The moisture causes the sugar to liquefy, rendering it useless as a bait carrier or an agent to extend the life of an active pesticide. Cellulose inert carriers such as ground corn cob, cornmeal, peanut hulls, paper or mineral carriers such as clay, silica, etc., do not dissolve like sugar but they attract moisture, displacing and or chemically reacting with the pesticide, reducing the usefulness of the carrier. By treating the carrier with a water repelling agent, the above problems are eliminated or delayed so as to extend the activity and usefulness of the carrier.

Considerations that must be dealt with in selecting the water repelling agent for a solid carrier such as a bait or a granule are:

1. Palatability and/or allowing the active ingredient to be accessible to the targeted pest.
2. The ability to be solvated and consumed by the targeted pest.
3. High water repellency allowing for low use levels.
4. The agent must prevent the carrier from compacting or caking when contacted with water.
5. The agent must be inert with the active ingredients.
6. The agent must be nontoxic and biodegradable.
7. The agent should fit easily into existing manufacturing processes.

While there are many water repelling compounds such as silicones, waxes, polymers, metal salts of fatty acids, various oils and so on, they all have one or more shortcoming. It has been discovered that sucrose, sorbitol, sorbinose, glycerol and raffinose poly esters of various fatty acids are palatable to most pests and will render most substrates hydrophobic. Di- and tri-esters with very low or no mono-ester percentages are very hydrophobic and effect water repellency at low concentrations. Sweetness is part of the molecule helping to make them very palatable to the pest. The fatty acids are long chain carbons with no volatility at room temperature. The esters will not react with the pesticides, attractants or the inerts normally found in solid pesticidal compositions such as baits or granules. They are stable, nontoxic and biodegradable. The esters used for imparting water resistance are solid at room temperature.

DETAILED DESCRIPTION OF THE INVENTION

EXAMPLE 1

| Fly Bait | Percentages |
| --- | --- |
| Methomyl | 1.000 |
| Z-9-tricosene | .025 |
| Sugar | 96.975 |
| Sucrose Distearate* | 2.000 |

*Crodesta F-10 — Croda Inc.

Manufacturing Procedure

1. Add to a ribbon, conical or other mixer which has the capability of being heated and will provide gentle mixing.
2. Pre-blend the methomyl and Z-9-tricosene in a suitable solvent (1,1,1 Trichloroethane) of sufficient volume to allow the methomyl and Z-9-tricosene to be sprayed onto the sugar while it is being mixed.
3. Continue mixing until the solvent has evaporated.
4. Add the sucrose ester and mix until uniformly mixed.
5. Heat mix to 70 degrees C. and blend for a short period and then cool to room temperature.

Water resistance was evaluated on the bait prepared in Example 1 versus the same formula without the sucrose ester included.

The products were tested as follows:

1. Two containers were filled with water at 24 degrees C.± to the same levels.
2. Five grams each of the treated and the untreated bait were added to the above containers respectively.
3. Visual observations were recorded as follows:

|  | Treated | Untreated |
|---|---|---|
| Initial | 90+% Floated | 100% went to bottom |
| 15 minutes | <5% in solution | >50% in solution |
| 30 minutes | <10% in solution | >75% in solution |
| 1 hour | <10% in solution | >90% in solution |
| 48 hours | <50% in solution | 100% in solution |

Palatability and repellency were evaluated on the same formulas as follows: One gram each of the treated and untreated bait was placed on paper plates respectively and placed in an area where there was sufficient fly pressure to allow for evaluation. Visual observations made were: 1.) No difference was observed in the way flies were attracted to the baits or in the way they feed on the baits. 2.) Visually, an equal number of flies were killed by each bait.

EXAMPLE 2

| Fly Bait | Percentages |
|---|---|
| Methomyl | 1.000 |
| Z-9-tricosene | .025 |
| Sugar | 97.475 |
| Acetylated Sucrose Distearate* | 1.500 |

*Crodesta A-10 — Croda Inc.

Manufacturing procedures outlined in Example 1 were followed, with the exception of heating the blend to 50 degrees C. instead of 70 degrees C.

EXAMPLE 3

| Snail Bait | Percentages |
|---|---|
| Metaldehyde | 3.25 |
| Corn cob meal | 93.75 |
| Sorbitol Tristearate | 3.00 |

Manufacturing Procedure
 1. Add to a jacketed ribbon blender the corn cob meal.
 2. Evenly apply the metaldehyde to the corn cob meal while gently blending.
 3. Evenly apply the sorbitol ester to the mix while gently blending.
 4. When mix is uniform, heat to 70 degrees C. for a short period of time and then cool to room temperature.

EXAMPLE 4

| Ant Bait | Percentages |
|---|---|
| Diazinon | .10 |
| Cornmeal | 96.90 |
| Glycerol Trioleate | 3.00 |

Manufacturing Procedure
 1. Add to a jacketed ribbon blender the corn meal.
 2. Evenly apply the diazinon to the cornmeal while gently blending.
 3. Evenly apply the glycerol trioleate to the mix while gently blending.
 4. When mix is uniform, heat to 70 degrees C. for a short period of time and then cool to room temperature.

EXAMPLE 5

| Rat Bait | Percentages |
|---|---|
| Warfarin | .025 |
| Cornmeal | 48.500 |
| Oatmeal | 48.475 |
| Sucrose Distearate | 3.000 |

Manufacturing procedure same as in Example 4.

Anti-caking was demonstrated by comparing an insecticide granule treated with sorbitol tristearate and the same formula granule without sorbitol tristearate after they had been completely submersed under water for twenty four hours, then allowed to dry completely. When the container of the sorbitol triester treated granules was turned upside down the granules fell out as individual granules. When the container of the untreated granules was turned upside down the granules did not fall out; they were stuck together and to the container.

EXAMPLE 6

| Fire Ant Granules for Outside Electronic Equipment | Percentages |
|---|---|
| Diethylene Glycol | 5.0 |
| Dursban HF | 8.0 |
| Aqsorb 18/16L LVM-MS | 84.0 |
| Sorbitol Tristearate | 3.0 |

Manufacturing Procedure
 1. Preblend diethylene glycol and Dursban HF.
 2. Charge blender with Aqsorb.
 3. While blending spray the preblended diethylene glycol and Dursban on to the Aqsorb granules.
 4. Add the sorbitol tristearate and mix until homogenous.
 5. Apply heat to blender until the granule temperature reaches 170 degrees Fahrenheit; mix until all granules are coated.
 6. Cool to room temperature and package.

EXAMPLE 7

| Mole Cricket Bait | Percentages |
|---|---|
| Peanut Hulls | 94.95 |
| Deltamethrin | .05 |
| Glycerol Trioleate | 5.00 |

EXAMPLE 8

| Yard Flea and Tick Granule | Percentages |
|---|---|
| Biodac 20/40 (paper) | 95.9 |
| E-Tox | .1 |
| Permethrin | 1.0 |
| Sorbitol tristearate | 3.0 |

EXAMPLE 9

| Vegetable Garden Dust | Percentages |
|---|---|
| Diatomaceous Earth | 94.0 |
| Pyrethrum | .5 |

| Vegetable Garden Dust | Percentages |
|---|---|
| Piperonyl butoxide | 2.5 |
| Sorbitol tristearate | 3.0 |

All percentages herein are by weight.

The word "pesticide" is used herein to include insecticides, acaricides, insect repellents and attractants, nematicides, insect growth regulators and rodenticides. Examples of pesticides suitable for the compositions of the present invention are: pyrethroids such as natural pyrethrins, allethrin, tetramethrin, resmethrin, fenothrin, permethrin, deltamethrin, tralomethrin and fenvalerate; growth regulators such as hydroprene, methoprene and diflubenzuron; organo phosphates and thiophosphates such as trichlorfon, naled, dichlorvos, mevinphos, demeton, malathion, dimethoate, acephate, fenthion, diazinon, phosmet and chlorpyrifos; attractants such as muscalure, hexalure and medlure; repellents such as ethyl hexanediol and deer; carbamates such as carbaryl, propoxur, bendiocarb, methomyl and aldicarb; and rodenticides such as warfarin.

Suitable water resistant coating agents for use in the present invention include long chain fatty acid poly esters of sucrose, sorbitol, sorbinose, glycerol and raffinose, which melt at above room temperature. Preferably the poly esters are di- or tri- esters with no or a low percentage of mono-esters. Suitable long chain fatty acids include saturated and unsaturated acids such as linolinic, palmitic, stearic and oleic. Generally, the fatty acid will have a chain length of about 12–22 carbon atoms. Mixed esters can be used also. Suitable procedures for preparing the esters are described in U.S. Pat. No. 3,480,616, the disclosure of which is incorporated herein by reference.

What is claimed is:

1. A water resistant solid pesticide composition which comprises:
   a solid pesticide carrier on which there has been applied a pesticide and
   a coating on said pesticide treated solid carrier of polyols selected from the group consisting of a long chain fatty acid poly ester of sucrose, sorbitol, sorbinose, glycerol, or raffinose.

2. A composition according to claim 1 wherein the solid pesticide carrier is a bait or granule.

3. A composition according to claim 2 wherein the pesticide is an insecticide and the carrier is a bait.

4. A composition according to claim 2 wherein the pesticide is an insecticide and the carrier is a granule.

5. A composition according to claim 3 wherein the poly ester is a di- or tri-ester.

6. A composition according to claim 5 wherein the ester is a sucrose di-ester.

7. A composition according to claim 5 wherein the ester is a sorbitol tri-ester.

8. A composition according to claim 5 wherein the ester is a glycerol tri-ester.

9. A composition according to claim 4 wherein the poly ester is a di- or tri-ester.

10. A composition according to claim 9 wherein the ester is a sucrose di-ester.

11. A composition according to claim 9 wherein the ester is a sorbitol tri-ester.

12. A composition according to claim 9 wherein the ester is a glycerol tri-ester.

13. A composition according to claim 2 wherein the pesticide is an insecticide and the ester is sucrose distearate.

14. A composition according to claim 2 wherein the pesticide is an insecticide and- the ester is sorbitol tristearate.

15. A composition according to claim 2 wherein the pesticide is an insecticide and the ester is glycerol trioleate.

16. A composition according to claim 2 wherein the pesticide is a carbamate insecticide and the ester is a di- or tri-ester.

17. A composition according to claim 2 Wherein the pesticide is a phosphate or thiophosphate insecticide and the ester is a di-or tri-ester.

18. A composition according to claim 2 wherein the pesticide is pyrethrum or a synthetic pyrethroid and the ester is a di- or tri-ester.

19. A composition according to claim 16 wherein the ester is a sucrose di-ester.

20. A composition according to claim 16 wherein the ester is a sorbitol tri-ester.

* * * * *